United States Patent [19]

Balmer

[11] Patent Number: 5,437,841
[45] Date of Patent: Aug. 1, 1995

[54] CUVETTE

[75] Inventor: Alfons Balmer, Steinhausen, Switzerland

[73] Assignee: Hoffmann-La Roche Inc., Nutley, N.J.

[21] Appl. No.: 184,521

[22] Filed: Jan. 21, 1994

Related U.S. Application Data

[63] Continuation of Ser. No. 880,149, May 7, 1992, abandoned.

[30] Foreign Application Priority Data

May 7, 1991 [CH] Switzerland ............ 1368/91

[51] Int. Cl.6 .................................. B01L 3/00
[52] U.S. Cl. ................... 422/102; 356/246; 422/104
[58] Field of Search ............ 356/246; 422/102, 104, 422/58; 220/608, 737; 206/514–520

[56] References Cited

U.S. PATENT DOCUMENTS

| | | | |
|---|---|---|---|
| 3,627,432 | 12/1971 | Bergmann | 356/246 |
| 3,684,453 | 8/1972 | Lartigue et al. | |
| 3,994,594 | 11/1976 | Sandrock et al. | 356/246 |
| 4,024,857 | 5/1977 | Blecher et al. | 128/2 F |
| 4,043,678 | 8/1977 | Farrell et al. | 356/246 |
| 4,119,407 | 10/1978 | Goldstein et al. | 422/58 |
| 4,263,256 | 4/1981 | Morle | 422/66 |
| 4,332,471 | 6/1982 | Gross | 356/246 |
| 4,371,498 | 2/1983 | Scordato et al. | 422/102 |
| 4,628,036 | 12/1986 | Scheepens et al. | 436/520 |
| 4,634,576 | 1/1987 | Galle et al. | 356/246 X |
| 4,639,135 | 1/1987 | Borer et al. | 356/246 |
| 4,659,550 | 4/1987 | Schildknecht | 422/73 |
| 4,799,599 | 1/1989 | Herrmann | 356/246 X |
| 4,871,674 | 10/1989 | Matsui et al. | 435/284 |
| 5,098,661 | 3/1992 | Froehlich et al. | 422/102 |

FOREIGN PATENT DOCUMENTS 152964 2/1985 European Pat. Off. .
90/05903 5/1990 WIPO .

Primary Examiner—Robert J. Warden
Assistant Examiner—Krisanne M. Thornton
Attorney, Agent, or Firm—George M. Gould; George W. Johnston; John P. Parise

[57] ABSTRACT

A cell for performing optical measurements in a automatic analyzer includes a cell having a tubular body. The body has two plane-parallel walls, and is open at one end and closed at the opposite end by a bottom wall. At the open end of the body, tongues extend perpendicularly outward from each plane-parallel wall. Each tongue includes a recess, with each tongue and its recess being symmetrically placed relative to another tongue and its recess with respect to the longitudinal axis of the cell.

16 Claims, 6 Drawing Sheets

CUVETTE

This is a continuation of application Ser. No. 07/880,149, filed May 7, 1992, now abandoned.

BACKGROUND OF THE INVENTION

1. Field of the Invention

The invention relates to a cell for performing optical measurements in an automatic analyzer and more particularly a single cell for an analyzer for chemical analyses.

2. Description

Cells for performing optical measurements are conventionally charged with samples and reagents in the analyzer, and electro-optical analysis is carried out on the mixture of sample and reagent contained in the cell.

Analyzers are known which use single reaction cells, also called measuring cells which are placed on a suitable carrier in the analyzer by a mechanical, automatically-controlled transport device and are removed therefrom after use. In these analyzers each cell remains on the cell carrier for the entire period of the analysis. Transport of each cell to the cell carrier and its removal from the carrier therefore take place only once. The risk of a cell being lost during transport is therefore relatively low.

In modern analyzers, in which the attempt is made to achieve a high number of measurements per unit of time, in correspondingly short cycle times, it is desirable to carry out some of the steps of the analysis process (e.g., the addition of reagents to individual cells, carrying out mixing movements of the cells, and so on) outside the cell carrier, and to use the cell carrier predominantly for performing optical measurements on the mixtures of sample and reagent in the cells. For this purpose, the transport of each cell to the cell carrier and its removal from the carrier must be carried out a number of times. Also, the transport system must allow each cell to be transported between the cell carrier and different processing stations. In addition, some analysis systems operate with rotatable cell carriers. It thus may be desirable to transport the cells even when the cell carrier is rotating. Consequently, the risk of a cell going astray with such a flexible and repeated transport system is correspondingly higher.

In many applications, the loss of a cell in the analyzer system is unacceptable. In otherwise extensively automated analyzers, any possibility of cell losses during their transport would make it necessary to at least visually monitor the transport of the cells during the operation of the analyzer. This is practically impossible.

SUMMARY OF THE INVENTION

The invention concerns an optical cell for performing optical measurements in an automatic analyzer and more particularly a single cell for an analyzer for chemical analyses to allow its transportation within the analyzer without any risk of loss. This inventive cell is suitable for performing spectrophotometrical absorbance measurements of a sample reagent mixture contained in the cell and for performing fluorescence polarization measurements of that mixture.

According to an aspect of the invention, the cell is molded in one piece from a transparent plastic. It has a tubular body which has two plane-parallel walls and and which is open at one end and closed at the opposite end by a bottom wall. The walls are parallel to each other and to the longitudinal axis of the cell. Each of the plane-parallel walls at the open end of the body has a tongue member which extends outwardly from the edge of the open end in a direction perpendicular to the plane-parallel walls. Each tongue member has a recess of preselected dimensions in the tongue's surface, and the tongues and their recesses are positioned symmetrical relative to one another with respect to the longitudinal axis of the cell.

A main advantage of the inventive cell as compared with the prior art cells is that the uniquely configured and dimensioned tongues and the recesses in the tongues are capable of co-operating with a corresponding mechanical gripper of the transport system as to preclude any loss of cells during their transportation. The tongues and recesses are configured and dimensioned to matingly and releasably engage corresponding elements on the gripper. In this way the cell according to the invention allows fully automatic loss-free cell transport within the analyzer system, even if repeated transport of each cell is necessary between the cell carrier and different processing stations. This transport can if necessary be carried out with the cell carrier rotating. There is therefore no need to monitor the cell transport.

In a preferred embodiment of the inventive cell, the diameter of each recess is approximately half the dimension (i.e., length) of the tongue measured in the direction perpendicular to the plane-parallel walls.

In another preferred embodiment of the inventive cell, the depth of each recess is approximately half the dimension (i.e., thickness) of the tongue, measured in the direction parallel to the plane-parallel walls.

In another preferred embodiment of the inventive cell, each tongue has a zone situated between the circumference of its recess and an outer edge of the tongue. The zone has a flat surface which forms an angle of approximately 45° with a plane perpendicular to the longitudinal axis of the cell. This embodiment has the advantage that the special construction of the tongue makes cooperation between the tongue and the mechanical gripper easier.

In another preferred embodiment of the inventive cell the tubular body has two side-walls which extend between the plane-parallel walls, said side-walls each having an upper portion and a lower portion, the lower portion being adjacent to the bottom wall. The lower portion of each side-wall includes an elongated, leg-shaped outer projection (or rib member) which extends longitudinally between the upper portion of the side-wall and a point adjacent the bottom wall. The provision of this leg-shaped projection, made during the manufacturing process of the cell by injection moulding, makes the cell optically suitable for performing spectrophotometrical absorbance measurements as well as fluorescence polarization measurements.

In another preferred embodiment of the inventive cell, the bottom wall of the cell is configured in the shape of a half-cylinder projecting away from the cell. This shape of the bottom wall makes the cell particularly suitable for fluorescence polarization measurements.

BRIEF DESCRIPTION OF THE DRAWINGS

A preferred embodiment of the invention is described below with reference to the accompanying drawings wherein.

DETAILED DESCRIPTION OF THE PREFERRED EMBODIMENTS

Figure 1:
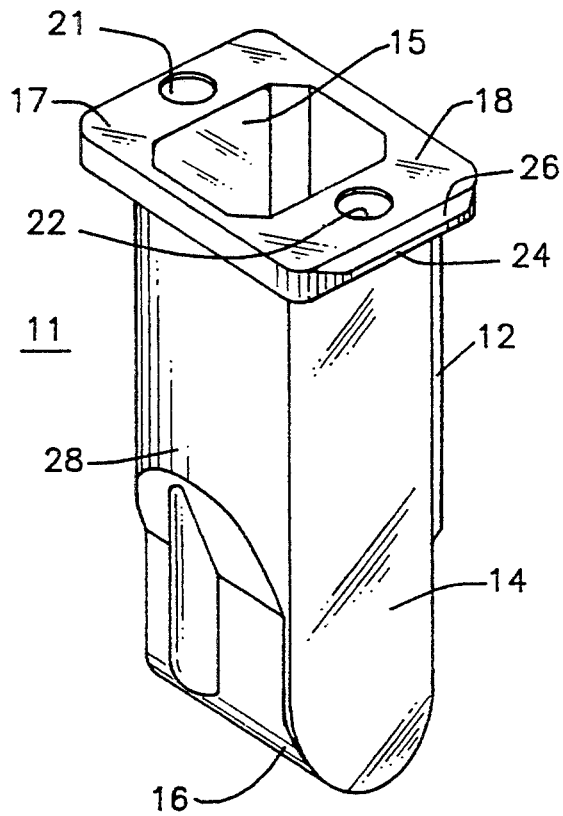
FIG. 1 is a perspective view of a cell according to the invention.
Figure 2:
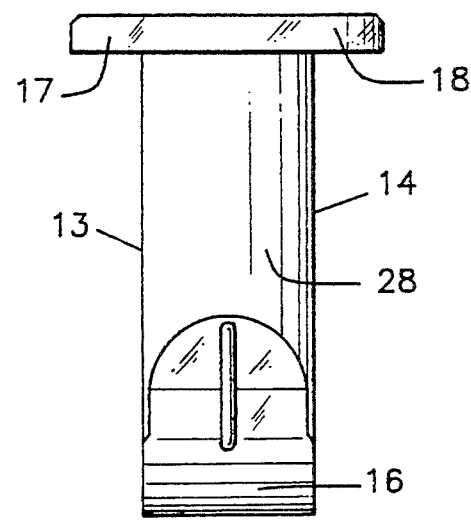
FIG. 2 is a first side elevation of the cell according to FIG. 1.

The present invention concerns a cell or cuvette for performing optical measurements in an automatic analyzer having a gripping means for transporting the cell. The cell is moulded in one piece from a transparent plastic material known in the art. According to the invention, the cell has a tubular body which includes two plane walls positioned parallel to each other and the longitudinal axis of the cell. The tubular body also has two opposite ends and a bottom wall. The first end is open to permit entrance of the sample reagent mixture to be measured. The second end is sealed by the bottom wall. Each of the plane-parallel walls adjacent the open end of the tubular body have a tongue member which extends outwardly from the open end in a direction perpendicular to the plane-parallel walls and ends at an outer edge. Each tongue has an upper surface and a recess. The recess is located in the upper surface. Each tongue and its corresponding recess is positioned symmetrical relative to the other tongue and recess with respect to the longitudinal axis of the cell. The dimensions of the tongue and its corresponding recess are preselected to permit cooperation with the gripping means by releasably securing the cell to the gripping means.

As shown in the accompanying drawings, cell 11 is a one-piece cuvette which is molded from a transparent plastic, (e.g. a polymethyl-methacrylate injection moulding material) by conventional techniques. The construction of this cell makes it suitable for performing optical measurements on the cell contents, which is usually a mixture of a sample and reagents.

The cell 11 has a tubular body 12, which has two plane-parallel walls 13, 14 and two side walls 27, 28, and which is open at one end 15 and closed by a bottom wall 16 at the opposite end. When optical measurements are carried out on the cell contents, a beam of light passes through and perpendicularly to the plane-parallel walls 13, 14. The plane-parallel walls are parallel to each other and are located along the longitudinal axis of the cell.

Each of the plane-parallel walls 13, 14 has a tongue 17, 18 located at the open end 15 of the body 12. Each tongue extends from the edge of open end 15 outwardly in a direction perpendicular to the plane-parallel walls 13, 14.

Each tongue 17, 18 has a recess 21, 22 of a preselected diameter and depth. The recesses are located on the upper surface of tongues 17 and 18, generally in the center of this surface. The tongues 17, 18 and their recesses 21, 22 are positioned symmetrical relatively to one another with respect to the longitudinal axis (Y—Y) of cell 11.

Figure 3:
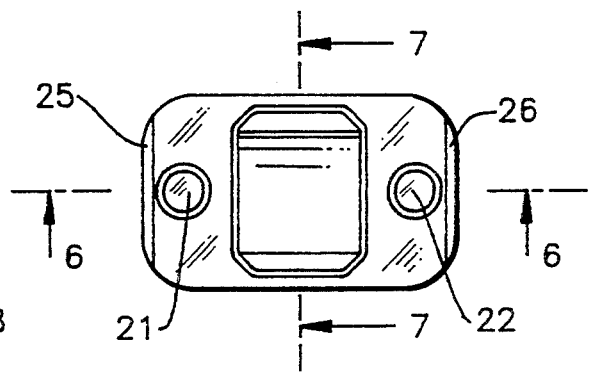
FIG. 3 is a plan view of the cell according to FIG. 1.
Figure 6:
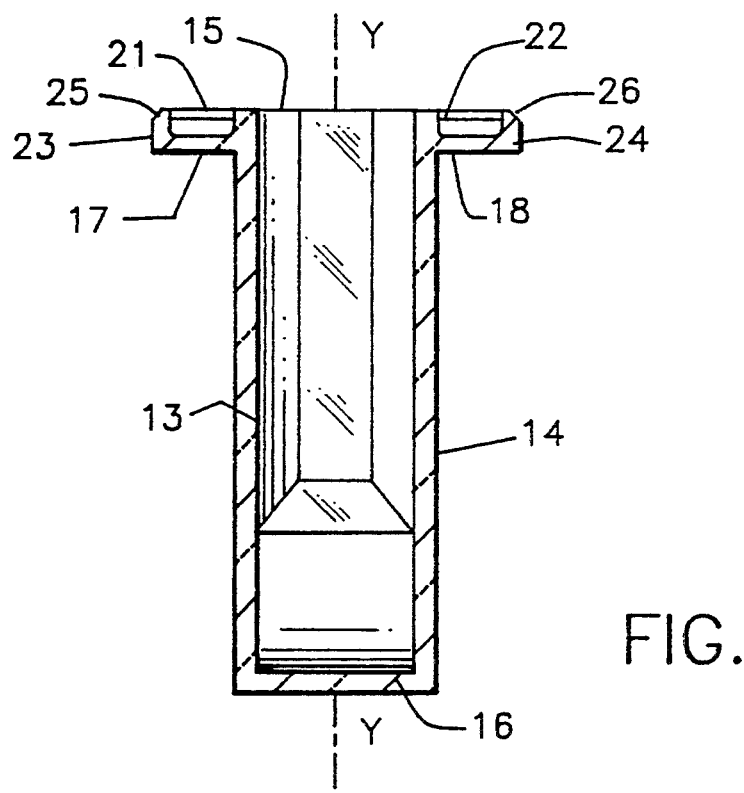
FIG. 6 is a cross-sectional view taken on the line 6—6 of FIG. 3.

In the preferred embodiment shown by FIGS. 3 and 6 the upper part of each of the recesses 21, 22 has the shape of a truncated cone, and the lower part of each recess has a cylindrical shape.

Figure 7:
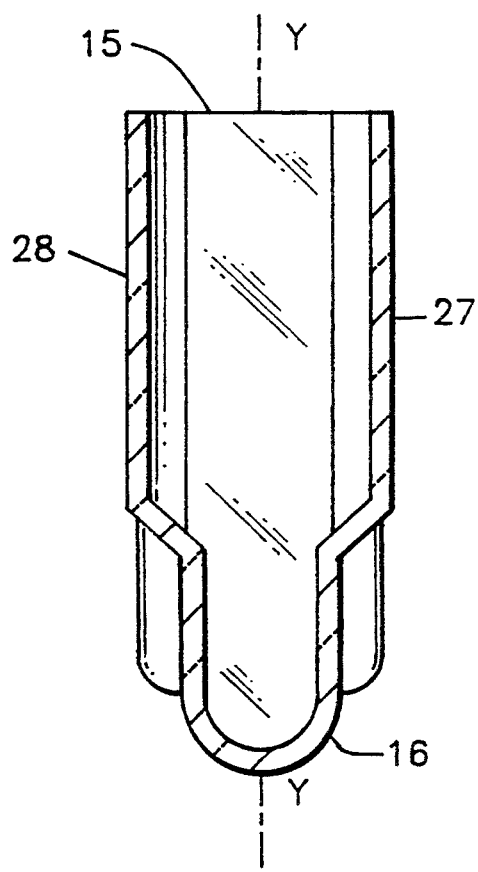
FIG. 7 is a cross-sectional view taken on the line 7—7 of FIG. 3.
Figure 8:
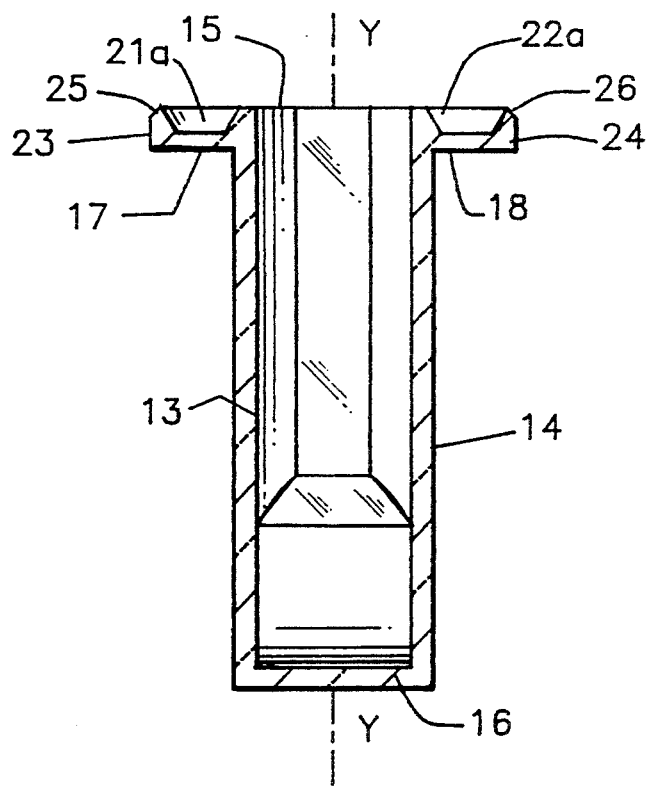
FIG. 8 is a cross-sectional view similar to the view shown by FIG. 6, but showing another embodiment of the cell.
Figure 9:
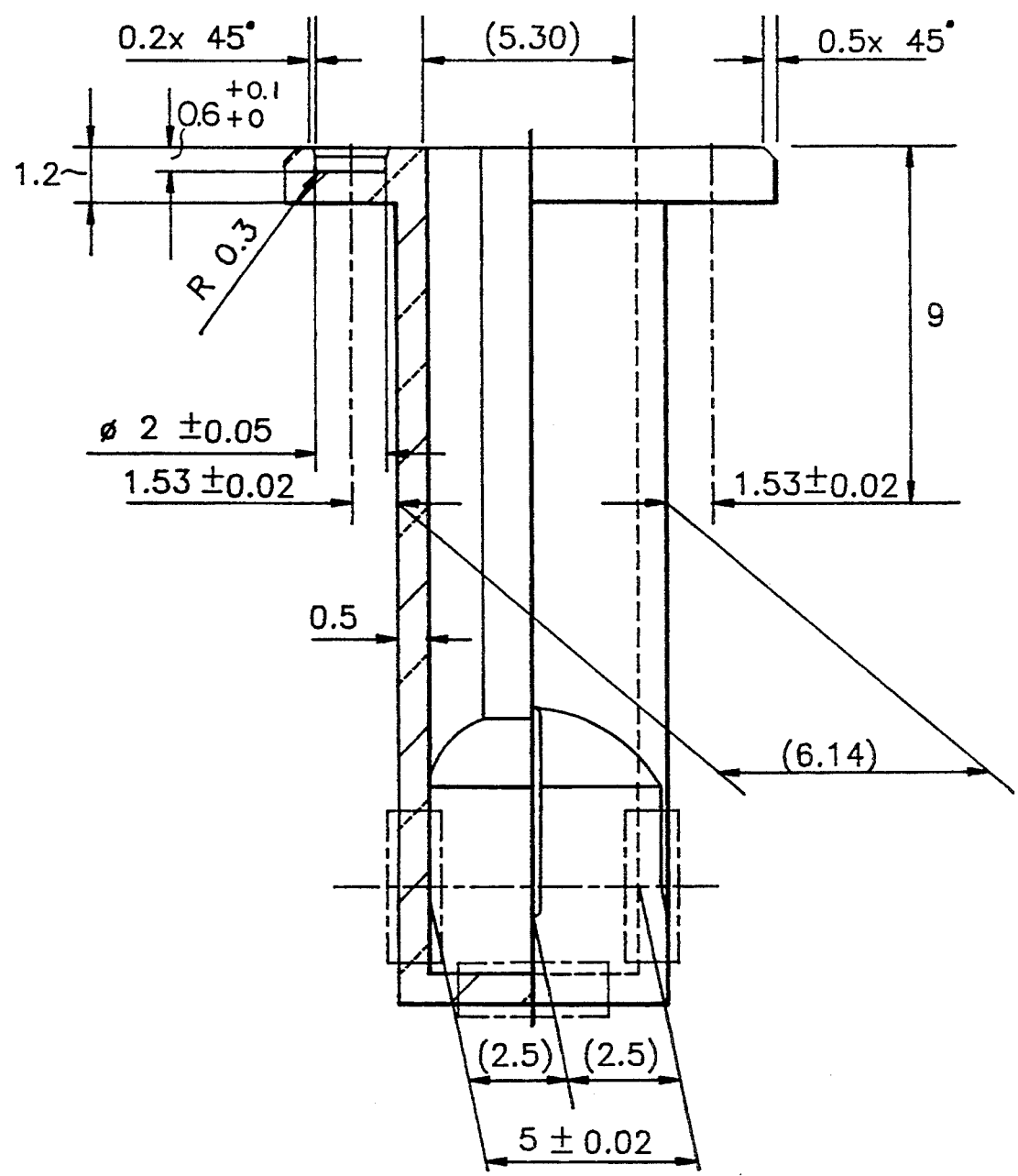
FIGS. 9–12 show views including dimentions of the cell according to FIGS. 1–7.
Figure 10:
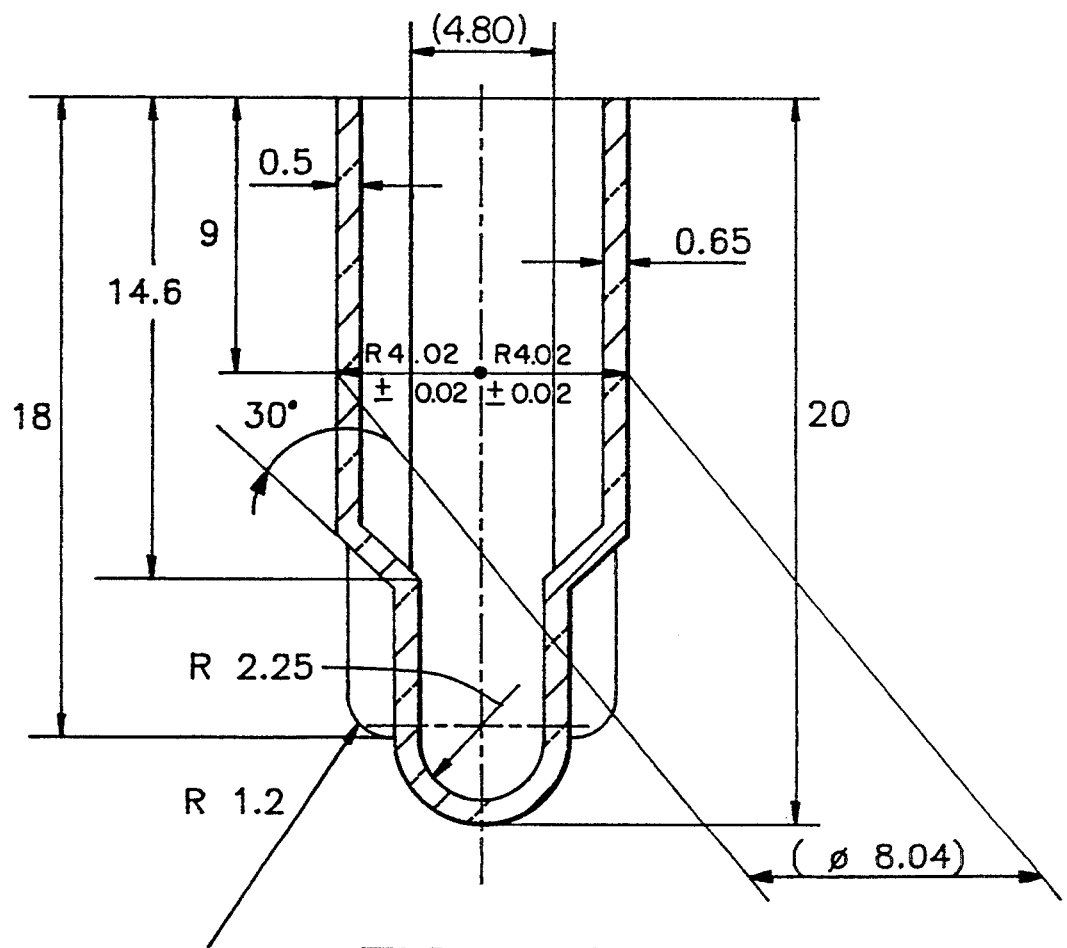
Figure 11:
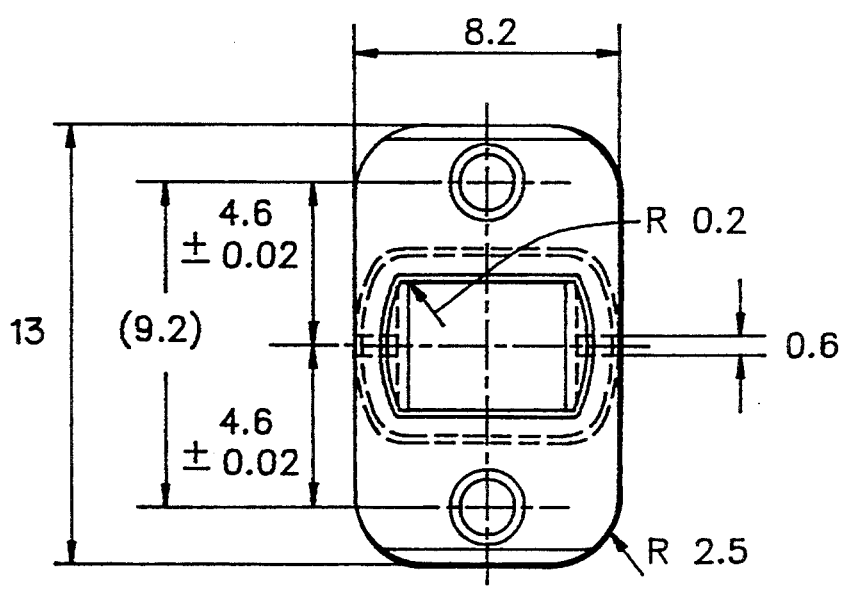
Figure 12:
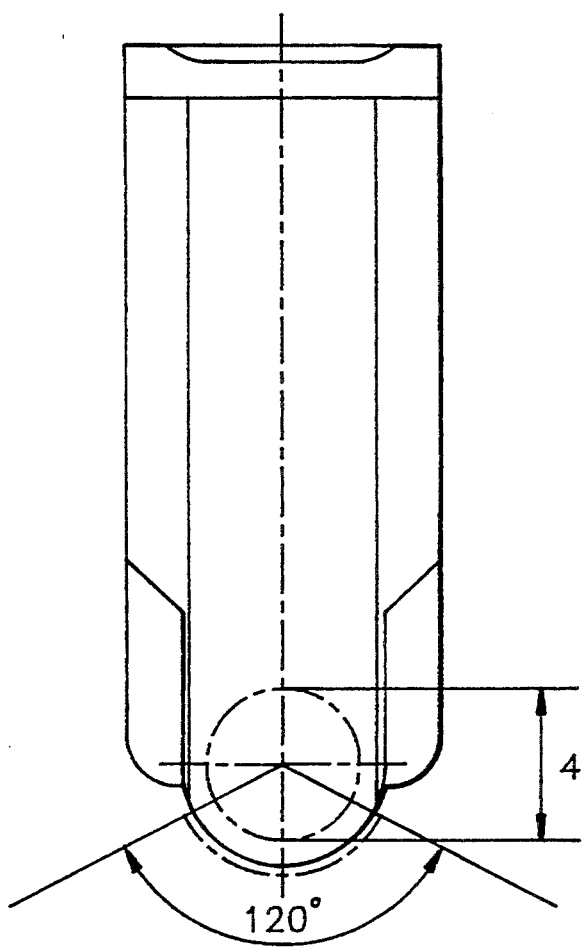

FIG. 8 shows a cross-sectional view similar to FIG. 6, but showing another preferred embodiment of the cell according to FIGS. 1–7. In the embodiment according to FIG. 8 each of the recesses 21a, 22a has the shape of a truncated cone. The average diameter of each of the recesses 21a, 22a is preferably approximately half the dimention of the tongue 17, 18 taken in the direction perpendicular to the plane-parallel walls 13, 14. All other features and dimentions of the embodiment according to FIG. 8 are the same as for the embodiment according to FIGS. 1–7.

The average diameter of each of the recesses 21, 22 is preferably approximately half the dimension of the tongue 17, 18 taken in the direction perpendicular to the plane-parallel walls 13, 14. This dimension is the length of the tongue taken between the open edge of open end 15 of tubular body 12 of cell 11 and outer edge 23 or 24 of the tongue. The depth of each of the recesses 21, 22 is preferably approximately half the dimension of the tongue 17 or 18 taken in the direction parallel to the plane-parallel walls 13, 14. This dimension is the thickness of the tongue.

Each tongue 17 and 18, has a zone located between the end (i.e., circumference) of its recess 21 or 22 and the outer edge 23, 24 of the tongue. Each zone preferably has a flat surface 25 or 26, which forms an angle of approximately 45° with a plane perpendicular to the longitudinal axis Y—Y of the cell.

The above-described construction of the cell 11 makes it optimally suitable for engagement by a gripper (not shown in the drawings) for example, in the form of tongs and forming a portion of a transport device. The gripper is adapted, by means of a conventional drive and appropriate control mechanism for the same, to releasably engage the cell in a predetermined withdrawal position, carry it to a predetermined delivery position, and deliver it there.

When the inventive cell is used for performing spectrophotometrical absorbance measurements of a sample-reagent mixture contained therein, a light beam is transmitted through the lower portion of plan-parallel walls 13, 14, which lower portion is adjacent to bottom wall 16. The lower portions of plane-parallel walls 13, 14, which are used as optical windows for the photometrical measurements, have to satisfy the prescribed optical requirements for performing such measurements.

Since the inventive cell can also be used for performing fluorescence polarization measurements and since for these measurements light leaving the cell through bottom wall 16 needs to be measured, this bottom wall has to satisfy the optical requirements for performing such measurements.

To obtain the desired accuracy when performing fluorescence polarization measurements, the change of light polarization introduced by the optical windows involved (i.e. the respective portions of the plane-parallel walls 13, 14 and the bottom wall 16 of the cell) has to be very low. To obtain this property, during the injection moulding process to make the cell, the location of the feeding point is chosen adjacent to the top edge of the cell (i.e. as far as possible from the lower portion of the cell where the optical windows are located). This choice causes however a confluence of material which is adverse to obtaining the desirable optical properties of the optical windows. It also creates difficulties when exhausting air which is present during the injection moulding process.

These difficulties are overcome by the following structure of the inventive cell. As shown by FIGS. 1, 2, 4, 5 and 7, the tubular body 12 has two side-walls 27, 28 which extend between the plane-parallel walls 13, 14. The side-walls 27, 28 each have an upper portion and a lower portion. The lower portion is adjacent the bottom wall 16. The lower portion of each side-wall 27 or 28 includes an elongated, leg-shaped outer projection 31, 32 (or rib member) which extends longitudinally between the upper portion of the side-wall and a point adjacent the bottom wall 16.

By including leg-shaped projections 31, 32 during the manufacturing process of the cell, it makes it possible to avoid the above-mentioned disadvantageous material confluence during the injection moulding process and thereby satisfy the optical requirements on the optical windows in both the plane-parallel walls 13, 14 and the bottom wall 16 for performing spectrophotometrical absorbance measurements as well as fluorescence polarization measurements.

To make the exhaustion of air possible during the injection moulding process, projections 31, 32 have a groove positioned along the longitudinal length of the leg and of a preselected narrow dimension (not shown in the enclosed drawings).

Figure 4:
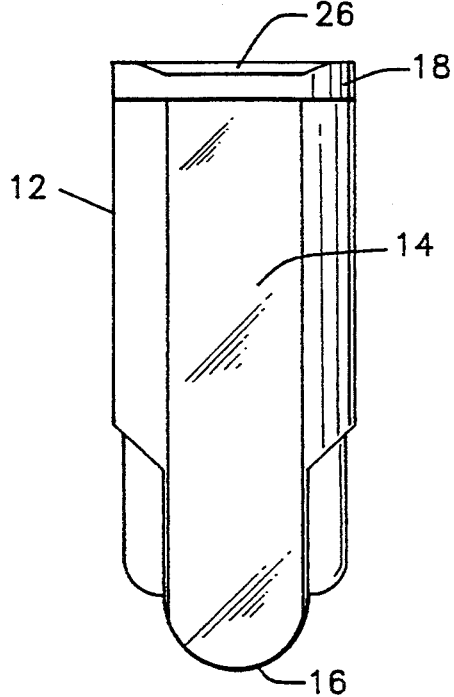
FIG. 4 is a second side elevation of the cell according to FIG. 1.
Figure 5:
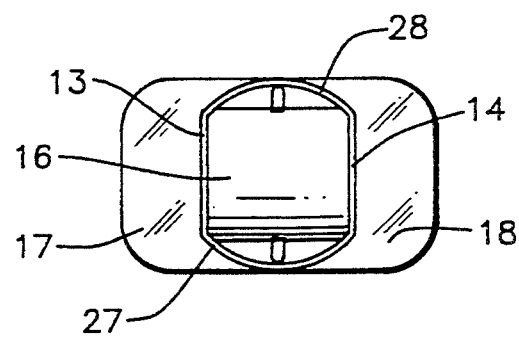
FIG. 5 is a bottom plan view of the cell according to FIG. 1.

As shown by FIGS. 1, 4 and 7, the bottom wall 16 of the cell has the shape of a half-cylinder wherein the half-cylinder projects outwardly away from tubular body 12. This shape of the bottom wall makes the cell particularly suitable for fluorescence polarization measurements. The necessary computations are simplified by the fact that the exciting light beam has a circular cross-section of a preselected value and the bottom wall 16 is cylindrical.

FIGS. 9–12 indicate specific dimentions in millimeters of the cell described above with reference to FIGS. 1–7.

While the invention has been described in conjunction with certain embodiments, it is understood that various modifications and changes may be made without departing from the spirit and scope of the invention. For example, the position and/or relative dimensions of the tongues and recesses may be modified provided they continue to cooperate with the gripper and can be releasably engaged by the gripper. Moreover, the geometric configuration of the tongue and its recess may be modified subject to the above requirements.

I claim:

1. A cell for performing optical measurements in an automatic analyzer having a griping means for transporting the cell, which comprises:
    (a) a tubular body having (i) two opposite ends, (ii) two plane-parallel walls positioned parallel to each other and to the longitudinal axis of the cell, said walls extending between said two opposite ends, and (iii) a bottom wall having the shape of a half-cylinder of a preselected diameter, projecting away from the tubular body, the first opposite end being open and the second opposite end being closed by the bottom wall;
    (b) each of the plane-parallel walls at the open end of the tubular body having a tongue which extends outwardly from the open end in a direction perpendicular to the plane-parallel wall and ending at an outer edge;
    (c) each tongue having an upper surface and a recess;
    (d) each tongue and its recess being positioned symmetrically relative to the other tongue and its recess with respect to the longitudinal axis of the cell; and
    (e) said cell having a one piece molded construction of transparent plastic material, and being constructed and arranged such that the dimensions of each tongue and its corresponding recess are preselected to permit cooperation with a gripping means to releasably engage therewith.

2. The cell of claim 1, wherein the recesses each have an upper part and a lower part, the upper part of each recess having the shape of a truncated cone, and the lower part of each recess having a cylindrical shape.

3. The cell of claim 1, wherein each of the recesses has the shape of a truncated cone.

4. The cell of claim 1, wherein the maximal width of each recess measured in the direction perpendicular to the plane parallel walls is approximately half the length of the corresponding tongue measured in the direction perpendicular to the plane parallel walls.

5. The cell of claim 1, wherein the depth of each recess is approximately half the thickness of the tongue measured in the direction parallel to the plane-parallel walls.

6. The cell of claim 1, wherein each tongue has a zone situated between its recess and the outer edge of the tongue, the zone having a flat upper surface which forms a preselected angle with a plane perpendicular to the longitudinal axis of the cell.

7. The cell of claim 6, wherein the preselected angle is approximately 45°.

8. The cell of claim 1, wherein the tubular body also has two side-walls each having an upper portion and a lower portion, the lower portion being adjacent the bottom wall.

9. The cell of claim 8, wherein the lower portion of each side-wall includes an elongated outer projection which extends between the upper portion of the side-wall and a point adjacent the bottom wall along the longitudinal axis of the cell.

10. The cell of claim 1, wherein the recesses each have an upper part and a lower part, the upper part of each recess having the shape of a truncated cone, and the lower part of each recess having a cylindrical shape.

11. A cell for performing optical measurements in an automatic analyzer having a gripping means for transporting the cell, which comprises:
    (a) a tubular body having (i) two opposite ends, (ii) two plane-parallel walls positioned parallel to each other and to the longitudinal axis of the cell, said walls extending between said two opposite ends, (iii) two side walls extending between the plane-parallel walls, and (iv) a bottom wall having the shape of a half-cylinder of a preselected diameter, projecting away from the tubular body, the first opposite end being open and the second opposite end being closed by the bottom wall;
    (b) two tongues located adjacent to the tubular body and extending outwardly from the open end in a direction perpendicular to the plane-parallel walls and ending at an outer edge;

(c) each tongue having an upper surface and a recess;

(d) each tongue and its corresponding recess being positioned symmetrically relative to the other tongue and its recess with respect to the longitudinal axis of the cell;

(e) each tongue having a zone situated between the recess and the outer edge of the tongue, the zone having a flat surface adjacent the outer edge, which forms a preselected angle with the plane perpendicular to the longitudinal axis of the cell;

(f) the side walls having an upper and lower portion, and an elongated outer projection which extends between the upper portion of the side wall and a point adjacent to the bottom wall of the tubular body;

(g) said cell having a one piece molded construction of transparent plastic material, and being constructed and arranged such that the dimensions of each tongue and its corresponding recess are preselected to permit cooperation with a gripping means to releasably engage therewith.

12. The cell of claim 11, wherein each of the recesses has the shape of a truncated cone.

13. The cell of claim 1, wherein each tongue has one recess.

14. The cell of claim 13, wherein each recess is located substantially in the center of the upper surface of each tongue.

15. The cell of claim 11, wherein each tongue has one recess.

16. The cell of claim 15, wherein each recess is located substantially in the center of the upper surface of each tongue.

* * * * *